United States Patent [19]

Religa et al.

[11] Patent Number: 5,449,385
[45] Date of Patent: Sep. 12, 1995

[54] SUPPORT FOR A HEART VALVE PROSTHESIS

[75] Inventors: Zbigniew Religa, Warsaw; Bogdan Stolarzewicz, Katowice; Romuald Cichon, Bytom; Marek Krzyskow, Swietochlowice; Jolanta Stozek, Katowice, all of Poland

[73] Assignee: Nika Health Products Limited, Vaduz, Liechtenstein

[21] Appl. No.: 146,035
[22] PCT Filed: May 8, 1992
[86] PCT No.: PCT/EP92/01017
§ 371 Date: Jan. 14, 1994
§ 102(e) Date: Jan. 14, 1994
[87] PCT Pub. No.: WO92/19184
PCT Pub. Date: Nov. 12, 1992

[30] Foreign Application Priority Data

May 8, 1991 [EP] European Pat. Off. ............ 91107446

[51] Int. Cl.⁶ .................................................. A61F 2/24
[52] U.S. Cl. ......................................... 623/2; 623/900
[58] Field of Search ..................................... 623/2, 900

[56] References Cited

U.S. PATENT DOCUMENTS

| 3,548,418 | 5/1968 | Angell et al. | 623/2 |
|---|---|---|---|
| 3,570,014 | 3/1971 | Hancock. | |
| 3,755,823 | 9/1973 | Hancock. | |
| 3,938,197 | 2/1976 | Milo. | |
| 3,983,581 | 10/1976 | Angell et al. | 623/2 |
| 4,259,753 | 4/1981 | Liotta et al. | |
| 4,364,127 | 12/1981 | Pierce et al. | |
| 4,626,255 | 12/1986 | Reichart et al. | 623/2 |
| 4,816,029 | 3/1989 | Penny, III et al. | 623/2 |
| 4,892,541 | 1/1990 | Alonso | 623/2 |
| 5,037,434 | 8/1991 | Lane | 623/2 |
| 5,326,370 | 7/1994 | Love et al. | 623/2 |

FOREIGN PATENT DOCUMENTS

| 0143246 | 9/1984 | European Pat. Off. . | |
|---|---|---|---|
| 155245 | 9/1985 | European Pat. Off. | 623/2 |
| 2451189 | 3/1980 | France. | |
| 1939121 | 8/1969 | Germany. | |
| 1264471 | 2/1972 | United Kingdom | 623/2 |
| 1264472 | 2/1972 | United Kingdom | 623/2 |
| 2159242 | 11/1985 | United Kingdom | 623/2 |
| 92013502 | 8/1992 | WIPO | 623/2 |

Primary Examiner—David Isabella
Assistant Examiner—Laura Fossum
Attorney, Agent, or Firm—Oliff & Berridge

[57] ABSTRACT

A heart valve prothesis is formed from a support having a textile covering. The support is formed from a single piece of flat, preferably thermoplastic material, arranged to form an annular structure, which preferably is either a hollow cylinder or a hollow cone.

21 Claims, 1 Drawing Sheet

SUPPORT FOR A HEART VALVE PROSTHESIS

BACKGROUND OF THE INVENTION

The invention relates to a support for a heart valve prothesis.

The known prostheses used in cardiac surgery contain a crown-shaped support of plastic, but generally of metal or of both materials. They consist in general of long, often wire-like elements which are predominantly not very elastic and are often joined by soldering or welding. This results in poor adaptability, especially since the joints then become brittle, but in some cases also relatively poor tolerance, not least because the textile covering generally applied to the support then requires several seams in order to hold securely on the wire skeleton of the support. This causes strength problems and also causes manufacture to be made more difficult. Typical heart valve prostheses of this type are described in U.S. Pat. No. 3,570,014 or U.S. Pat. No. 3,755,823.

SUMMARY OF THE INVENTION

It is the object of the invention to design a support for a heart valve prosthesis of the type described above in such a way that the adaptability and tolerance are improved, strength problems being avoided. This is achieved according to the invention by providing a support of plastic material for the heart valve prosthesis, the support having at one axial end, axially projecting support arms distributed over a circumference of the support and rounded at their free ends. A covering is provided over the support for fastening biological heart valve material. The support is formed as a single piece from flat, closed, preferably thermoplastic material that has an approximately hollow cylindrical or hollow conical shape.

The two-dimensional embodiment ensures both flexibility and adaptability, the one-piece embodiment making solder connections or the like superfluous, which is advantageous on the one hand for strength and durability and on the other hand for easier manufacture.

The elasticity and flexibility of the support arms is further improved by having the support wall thickness taper towards the free ends of the support arms. The provision of indentations between projections, permits the accommodation of excess biological heart valve material, which is fastened in a known manner to the support or to its textile covering. It is true that similar indentations were present-also in an embodiment according to U.S. Pat. No. 4,259,753, which attempted to overcome the previous disadvantages by avoiding long support arms, and of course with acceptance of the other disadvantages mentioned.

In particular, the embodiment, according to the invention, of the support provides such great adaptability that the heart valve prosthesis can be used equally, in the position of mitral or trichospidal valves.

BRIEF DESCRIPTION OF THE DRAWINGS

Further details of the invention are evident from the following description of embodiments shown schematically in the drawing.

DETAILED DESCRIPTION OF PREFERRED EMBODIMENTS

Figure 1:
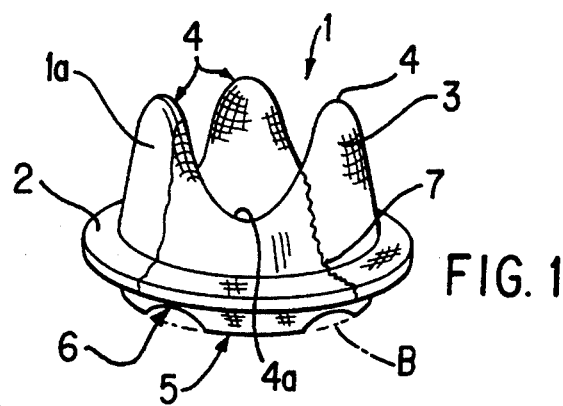
FIG. 1 shows a support according to the invention before attachment of the biological heart valve material and FIG. 2 shows the developed view of a support formed according to the invention.

FIG. 1 shows a heart valve prosthesis 1 having an annular support 1a according to the invention in an oblique view with partly removed textile covering 3, which covers the annular support 1a together with a collar 2 mounted thereon. As can be seen, the support 1a consists of flat material, in particular of a thermoplastic, so that it can be produced easily and economically, for example by injection molding.

The support 1a possesses, in a known manner, three axially projecting support arms 4, the free ends of which are rounded in the manner to be described subsequently with reference to FIG. 2. Projections 5 and indentations 6 are arranged alternately at the axial end of the support 1a, opposite the support arms 4, in which indentations any excess biological heart valve material, which is to be flattened in conventional manner over the support arms and is to be fastened to-the collar 2, can be accommodated. As will be explained subsequently, the support 1a—in contrast to the prior art—is relatively flexible and elastic, and expediently only the middle region between the base region 4a of the support arms 4 and the indentations 6 can be reinforced, as is evident from FIG. 4a and 5a.

The textile covering 3 is expediently elastic and consists, for example, of a network fabric, because such a fabric has sufficient intrinsic elasticity—even when conventional, biologically tolerated textile material is used. In practice, a USCI product, Adavison, from C. R. Bard, Catalogue No. 007831, has proved expedient. This is all the more surprising since nonelastic coverings have been chosen to date; however, it will subsequently become clear that the choice of elastic material results in a simplification in the manufacture of the heart valve prosthesis, improved safety with respect to tearing of seams and a smaller number of such seams, which also improves the tolerance of the prosthesis. This is because in many cases a concealed (and therefore invisible) circumferential seam in the region of the collar 2 will be sufficient, if necessary with a vertical seam 7.

Figure 2:
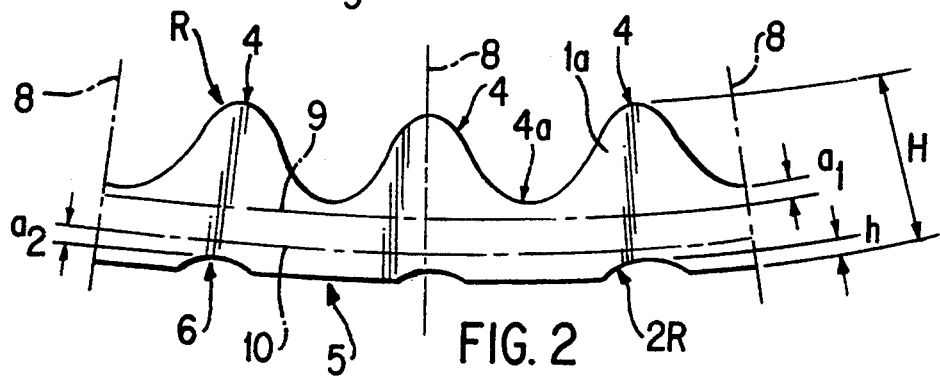

From the,developed view of the enclosed support 1a according to FIG. 2, it can be seen that the indentations 6 are located exactly opposite the support arms 4, on the same generatrix 8 which forms a common axis of symmetry. The rather flat projections 5 are located between the indentations 6. The generatrices 8 preferably form a gentle cone, the geometry of which will be discussed with reference to FIG. 3 to 5a. The height H from the outermost tip of the support arms 4 to the ends of the projections 5 is smaller than the maximum diameter of the support 1a shown in FIG. 1.

To make it easier to pull on the material 3—with an optimal anatomical fit—it is expedient if the support arms 4 are rounded at their free ends with a radius R which corresponds to not more than one eighth of the diameter of the support 1a—measured in the region of the collar 2 shown in FIG. 1. On the other hand, it is advantageous if the indentations 6 are relatively flat, the radius of curvature 2R preferably corresponding to not more than twice the radius of curvature R of the support arms 4. The collar 2 consisting of textile or plastic material is expediently mounted between the two circumferential lines 9 and 10, the circumferential line 9 being located underneath the base 4a of the support arms 4—preferably at a distance a1 of about 1 mm—the circumferential line 10 advantageously being located somewhat further, for example a distance a2 of about 2 mm, from the edges of the indentations 6. The height h of the indentations 6, that is to say the height of the arrow from the free end of the projections 5 to the lowest point of the indentation 6, should expediently be not more than 0.2 mm.

The wall thickness W of the flat support 1a can be relatively uniform and not more than 1 mm, but FIG. 3 to 5a are intended to show that nonuniform wall thicknesses are also possible within the scope of the invention. It should also be mentioned that FIG. 2 shows an equidistant arrangement of the support arms 4, i.e. an arrangement distributed symmetrically over the circumference of the annular element 1a, but that, as has also already been proposed—asymmetric arrangements are likewise possible. Thus, by means of different spacings between the support arms 4, the fact that the biological material is generally not uniformly available for the heart prosthesis is taken into account. For example, if the spacing of the three arms increases in the clockwise or counterclockwise direction, an angular sequence of 110°, 120° and 130° proving particularly advantageous, different biological circumstances can be catered for with these two embodiments.

Figure 3:
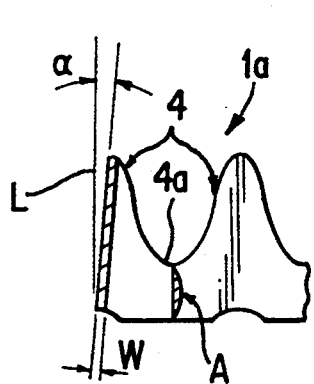
FIGS. 3 to 5a show various cross-sectional forms of the FIG. 2 support.

FIG. 3 shows a section through the support 1a, in which the arms 4 make an angle $\alpha$, preferably of not more than 8°, with a longitudinal axis or with a line L parallel thereto, so that the vertical angle of the support arms 4 converging from two opposite sides of the annular element 1a is finally $2\alpha$. In this embodiment, the wall thickness W in the region of the support arms 4 is relatively uniform; it may taper slightly towards the free ends of the arms 4, while the region located underneath the base 4a can be reinforced midway in its cross-section A, that is to say arched inwards. This gives the support arms 4 increased mobility and elasticity which supports its function at a point in constant movement and, owing to its greater adaptability, makes the prosthesis more suitable for use in a very wide range of positions.

Figure 4:
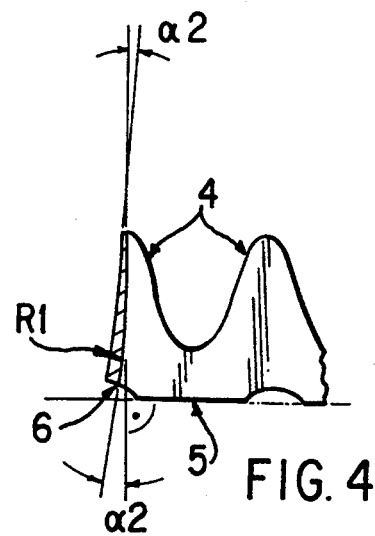

In the case of FIG. 4, too, the outer surface of the support arms 4 is conical with respect to the longitudinal axis of the support 1a, as is preferred. Here, however, the internal diameter of the support is the same over the height of the support arms 4, so that the inner cavity—in the region of the support arms 4—is to be regarded as cylindrical. In addition to this conical embodiment of the upper support arm region of the support 1a, the lower region too, which includes the projections 5 and the indentations 6, can be in the form of a cone which opens in a downward direction and has a slightly larger cone angle $\alpha 1$, where $\alpha 1$ may be, for example, about 2° larger than $\alpha$. If, for example, $\alpha$ is 6°, $\alpha 1$ is 8°.

The transition from the upper region of the support arms 4 to the lower region of the projections 5 is preferably via the outer (and inner) curvature. The radius R1 of this curvature is not critical and may be, for example, 15 to 45 mm. This also improves the retention of the collar 2—where it is used—and of course the transition from the upper to the lower region is therefore close to the line 10 described above with reference to FIG. 2.

Figure 4A:
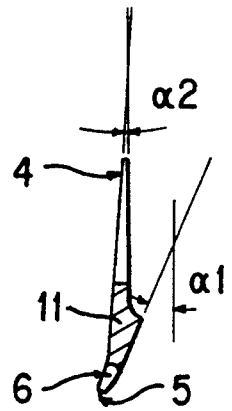

As shown in FIG. 4a by means of a section, an annular region 11 which has a cross-section tapering inwards to a point and imparts greater stability there to the support 1a while fully retaining the elasticity of the support arms, can be provided between the projecting support arms 4 and the projections 5 forming—similarly to FIG. 4—a lower cone of relatively great divergence. For reasons relating to medical technology, however, a continuously rounded transition is generally provided between the upper and the lower region. The fact that the wall thickness of the support arms 4 tapers at an angle $\alpha 2$ towards their free ends in such a way that the free end is, for example, about 20% narrower than the base of the particular support arm 4 helps to increase the elasticity in the case of FIG. 4 and 4a.

If FIG. 4a also shows an annular region 11 tapering inwards to a point, it is of course true that an inner curvature, for example having the stated radius R1, is preferable. Larger radii of, for example, 30 mm (cf. FIG. 5) are preferable to smaller radii (cf. FIG. 5a) because they permit better adaptation to the particular function. Thus, the embodiment according to FIG. 5 appears to be optimal; it has an upper cone having a vertical angle of, for example, 6° and a lower cone having a vertical angle of, for example, 8°, in conjunction with tapering of the support arms 4 towards their free ends, and an inner curvature having a radius R1.

In this sense, it is possible first to prefabricate supports 1a of different diameters, preferably from 17 mm to 33 mm at the base B. In order subsequently to form a heart valve prosthesis 1 shown in FIG. 1 therefrom, a textile covering 3 must be provided—in the manner described. In practice, a human (if desired also an animal) pulmonary or aortic valve is stored either in a nutrient solution (together with antibiotics and other substances) and is sewn to the prosthesis shown shortly before use; alternatively, the already combined components of the prosthesis are stored or frozen together in a nutrient solution until they are required. This also ensures a high rate of cell survival, and the prostheses produced in this manner can be used in four different positions.

Figure 5:
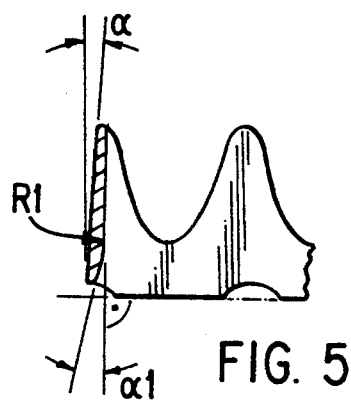
Figure 5A:
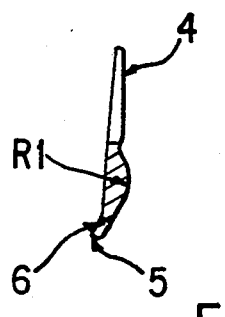

A large number of modifications are possible within the scope of the invention: although the tapering with the angle $\alpha 2$ (FIG. 4) was described with reference to the support arms 4, it is advantageous if the projections 5 also taper, as illustrated in particular by the preferred embodiment according to FIG. 5, with the result that these projections 5, too, impart improved elasticity.

We claim:

1. A support for a heart valve prosthesis, said support having a longitudinal axis, comprising:
   a hollow cylindrical structure having an annular reinforced region and first and second oppositely facing axial ends with respect to the longitudinal axis of the support;
   a plurality of axially projecting support arms distributed over a circumference of said hollow cylindrical structure at the first axial end, each support arm having a wall thickness that narrows from the annular reinforced region towards a free end; and
   a plurality of axially extending projections distributed over a circumference of said hollow cylindrical structure at the second axial end, each projection having a wall thickness that narrows from the annular reinforced region towards a free end, and an indentation being located between each projection.

2. The support according to claim 1, wherein the free ends of said plurality of support arms are rounded.

3. The support according to claim 2, wherein a radius of curvature by which the free ends of said plurality of support arms are rounded is not more than one eighth of a diameter of a base of said hollow cylindrical structure.

4. The support according to claim 2, wherein each indentation is rounded.

5. The support according to claim 4, wherein a radius of curvature by which each indentation is rounded is not more than twice a radius of curvature of the free ends of said plurality of support arms.

6. The support according to claim 1, wherein said plurality of support arms converge towards one another to form an upper cone.

7. The support according to claim 6, wherein said plurality of projections diverge from one another to form a lower cone.

8. The support according to claim 7, wherein an angle between the lower cone and the longitudinal axis of the support is greater than an angle between the upper cone and the longitudinal axis of the support.

9. The support according to claim 8, wherein said plurality of support arms converge conically at an angle of not more than approximately 6° with respect to the longitudinal axis of the support.

10. The support according to claim 8, wherein said plurality of projections diverge conically at an angle of not more than approximately 8° with respect to the longitudinal axis of the support.

11. The support according to claim 1, wherein a total height of said hollow cylindrical structure is not more than a diameter of said hollow cylindrical structure.

12. The support according to claim 11, wherein said diameter is between approximately 17 mm and 33 mm.

13. The support according to claim 1, wherein said annular reinforced region comprises a collar.

14. The support according to claim 13, wherein said collar is comprised of a textile material.

15. The support of claim 1, further comprising a covering over said hollow cylindrical structure for fastening the support to biological heart valve material.

16. The support according to claim 1, wherein a wall thickness of each support arm is not more than approximately 1 mm.

17. The support according to claim 1, wherein a wall thickness of each projection is not more than approximately 1 mm.

18. The support according to claim 1, wherein a height of the indentation between each projection is not more than approximately 0.2 mm.

19. The support according to claim 1, wherein said plurality of support arms are different distances apart around the circumference of said hollow cylindrical structure.

20. The support according to claim 1, wherein said annular reinforced region projects towards the longitudinal axis of the support.

21. The support according to claim 1, wherein said support comprises a single piece of thermoplastic material.

* * * * *